(12) United States Patent
Sivriver et al.

(10) Patent No.: US 12,392,039 B2
(45) Date of Patent: *Aug. 19, 2025

(54) PRE-INITIATED OPTICAL FIBERS AND METHODS OF MAKING THEREOF

(71) Applicant: BIOLASE MG LLC, Irvine, CA (US)

(72) Inventors: Alina Sivriver, Irvine, CA (US); Dmitri Boutoussov, Dana Point, CA (US)

(73) Assignee: BIOLASE MG LLC

( * ) Notice: Subject to any disclaimer, the term of this patent is extended or adjusted under 35 U.S.C. 154(b) by 600 days.

This patent is subject to a terminal disclaimer.

(21) Appl. No.: 17/529,007

(22) Filed: Nov. 17, 2021

(65) Prior Publication Data

US 2022/0186376 A1 Jun. 16, 2022

Related U.S. Application Data

(63) Continuation of application No. 16/658,612, filed on Oct. 21, 2019, now Pat. No. 11,193,209, which is a
(Continued)

(51) Int. Cl.
*C03C 25/60* (2018.01)
*A61B 18/22* (2006.01)
(Continued)

(52) U.S. Cl.
CPC .............. *C23C 18/14* (2013.01); *A61B 18/22* (2013.01); *C03C 25/1063* (2018.01);
(Continued)

(58) Field of Classification Search
CPC ....... C03C 25/60; C23C 18/14; C23C 18/143; C23C 13/182; C23C 20/04
See application file for complete search history.

(56) References Cited

U.S. PATENT DOCUMENTS 2,615,006 A 10/1952 Lane
3,821,510 A 6/1974 Muncheryan
(Continued)

FOREIGN PATENT DOCUMENTS

JP H06120609 A 4/1994
JP H09159880 A 6/1997
WO 2011082383 A2 7/2011

OTHER PUBLICATIONS

International Search Report and Written Opinion for International Application No. PCT/US2015/016962, May 22, 2015, 7 pages.
(Continued)

*Primary Examiner* — Erin Snelting

(57) ABSTRACT

Embodiments of the invention include a method of initiating an optical fiber of a tip assembly to form a finished tip assembly. In some embodiments, at least a portion of a distal portion of the optical fiber is coated with an energy absorbing initiating material. In some embodiments, the initiating material is an enamel material including a mixture of brass (copper and zinc) flakes or aluminum flakes in a solution of organic solvents. After the initiating material dries, a diode laser is fired through the optical fiber. The laser energy is at least partially absorbed in the initiating material and ignites the organic solvents. This combustion melts the material of the optical fiber, and impregnates the optical fiber with the metal flakes of the initiating material. The resulting initiated optical fiber is thus permanently modified so that the energy applied through the fiber is partially absorbed and converted to heat.

12 Claims, 2 Drawing Sheets

ISOMETRIC VIEW OF A SAMPLE DIODE TIP WITH THE INITIATION SITE CIRCLED

Related U.S. Application Data continuation of application No. 15/785,261, filed on Oct. 16, 2017, now Pat. No. 10,450,656, which is a continuation of application No. 14/628,083, filed on Feb. 20, 2015, now Pat. No. 9,788,899.

(60) Provisional application No. 61/942,385, filed on Feb. 20, 2014.

(51) Int. Cl.

| | | |
|---|---|---|
| *C03C 25/106* | (2018.01) | |
| *C23C 18/14* | (2006.01) | |
| *C23C 18/18* | (2006.01) | |
| *C23C 20/04* | (2006.01) | |
| *G02B 6/00* | (2006.01) | |
| *G02B 6/24* | (2006.01) | |
| *G02B 6/36* | (2006.01) | |
| *G02B 6/38* | (2006.01) | |

(52) U.S. Cl.
CPC ............ *C03C 25/60* (2013.01); *C23C 18/143* (2019.05); *C23C 18/182* (2013.01); *C23C 20/04* (2013.01); *G02B 6/00* (2013.01); *G02B 6/243* (2013.01); *G02B 6/3624* (2013.01); *A61B 2018/2222* (2013.01); *A61B 2018/2255* (2013.01); *G02B 6/381* (2013.01)

(56) References Cited

U.S. PATENT DOCUMENTS

| | | | |
|---|---|---|---|
| 4,620,994 | A | 11/1986 | Suss et al. |
| 4,770,811 | A | 9/1988 | Myers |
| 5,199,417 | A | 4/1993 | Muller et al. |
| 5,627,922 | A | 5/1997 | Kopelman et al. |
| 5,993,909 | A | 11/1999 | Mizutani et al. |
| 5,997,571 | A | 12/1999 | Farr et al. |
| 6,008,264 | A | 12/1999 | Ostler et al. |
| 6,384,099 | B1 | 5/2002 | Ostler et al. |
| 6,699,239 | B1 | 3/2004 | Stiller et al. |
| 7,621,745 | B2 | 11/2009 | Bornstein |
| 7,959,441 | B2 | 6/2011 | Glover et al. |
| 7,980,854 | B2 | 7/2011 | Glover et al. |
| 8,888,767 | B2 | 11/2014 | Neuberger et al. |
| 8,926,601 | B2 | 1/2015 | Neuberger et al. |
| 8,956,343 | B2 | 2/2015 | Belikov et al. |
| 9,551,839 | B2 | 1/2017 | Rollinger |
| 10,450,656 | B2 | 10/2019 | Sivriver et al. |
| 2003/0113075 | A1 | 6/2003 | Marquez et al. |
| 2004/0086004 | A1 | 5/2004 | Bonaccini et al. |
| 2004/0105163 | A1 | 6/2004 | Bryan et al. |
| 2005/0095356 | A1 | 5/2005 | Nakamura et al. |
| 2005/0244641 | A1 | 11/2005 | Vincent |
| 2007/0270788 | A1 | 11/2007 | Nahen et al. |
| 2008/0050702 | A1 | 2/2008 | Glover et al. |
| 2008/0058908 | A1 | 3/2008 | Bornstein |
| 2008/0070195 | A1 | 3/2008 | DiVito et al. |
| 2008/0077204 | A1 | 3/2008 | Bornstein |
| 2009/0220908 | A1 | 9/2009 | DiVito et al. |
| 2010/0330539 | A1 | 12/2010 | Glover et al. |
| 2011/0070552 | A1 | 3/2011 | Bornstein |
| 2011/0224660 | A1 | 9/2011 | Neuberger et al. |
| 2012/0057841 | A1 | 3/2012 | Wysocki et al. |
| 2012/0123399 | A1 | 5/2012 | Belikov et al. |
| 2013/0111953 | A1 | 5/2013 | Maloney et al. |
| 2013/0143180 | A1 | 6/2013 | Glover et al. |
| 2013/0310819 | A1 | 11/2013 | Neuberger et al. |
| 2014/0220511 | A1 | 8/2014 | DiVito et al. |
| 2016/0291256 | A1 | 10/2016 | Rollinger |
| 2017/0143987 | A1 | 5/2017 | Elman et al. |
| 2019/0196114 | A1 | 6/2019 | Yang |
| 2020/0008873 | A1 | 1/2020 | Pinnow |

OTHER PUBLICATIONS

R.J. Lewis Sr.; Hawley's Condensed Dictionary, 12th edition; Van Nostrand Reinhold Company, New York; 1993; pp. 671, 787, and 804-805.

R.J. Lewis Sr.; Hawley's Condensed Chemical Dictionary, 12th edition; Van Nostrand Reinhold Company, New York; 1993; pp. 122-123, 166, 462, and 659-660.

Julius Grant; Hackh's Chemical Dictionary, 3rd edition; McGraw-Hill Book Company; New York; 1944, pp. 101, 142, and 305.

Webster's Ninth New Collegiate Dictionary; Merriam-Webster's; Springfield, Massachusetts; 1990; pp. 133, 175, 409, and 1028.

Chinese Patent Office; Notification of the First Office Action, Issued in Connection to CN2015800096825; Jun. 28, 2017; 6 pages; China.

ISOMETRIC VIEW OF A SAMPLE DIODE TIP WITH THE INITIATION SITE CIRCLED

DIODE TIP WITH ENAMEL PAINT APPLIED TO END, CIRCLED

DIODE TIP IN THE PROCESS OF INITIATION

PRE-INITIATED OPTICAL FIBERS AND METHODS OF MAKING THEREOF

CROSS-REFERENCE TO RELATED APPLICATIONS

This is a continuation application of U.S. application Ser. No. 16/658,612, filed Oct. 21, 2019, entitled "PRE-INITIATED OPTICAL FIBERS AND METHODS OF MAKING THEREOF", which is a continuation application of U.S. application Ser. No. 15/785,261, filed Oct. 16, 2017, entitled "PRE-INITIATED OPTICAL FIBERS AND METHODS OF MAKING THEREOF", which is a continuation application of U.S. application Ser. No. 14/628,083, filed Feb. 20, 2015, entitled "PRE-INITIATED OPTICAL FIBERS FOR MEDICAL APPLICATIONS", which claims the benefit of and priority to U.S. Application No. 61/942,385, filed Feb. 20, 2014, entitled "PRE-INITIATED OPTICAL FIBERS FOR MEDICAL APPLICATIONS," the entire contents of which are incorporated herein by reference.

BACKGROUND OF THE INVENTION

1. Field of the Invention

Embodiments of the invention relate generally to medical laser systems and, more particularly, to a method of initiating an optical fiber of a tip assembly. The initiation employs the use of a metal colored enamel or initiating material that results in the finished, initiated optical fiber being impregnated with metal particles or flakes. The adhesion or bond of the metal particles or flakes to the optical fiber is superior to that of carbon based materials, non-organic, synthetic, or non-metal based pigments impregnated into optical fibers in accordance with existing initiation techniques.

2. Background

Lasers find application in a variety of medical and dental treatment procedures, where some of the most common operations involve cutting, ablation, disinfection, or other treatment of tissue. Depending on the particular wavelength, output power, and pulse width of the laser emission, as well as the absorptivity of the target tissue, varying biological materials from soft tissue such as muscles and skin, to hard tissue such as teeth and bones, can be cut and ablated. Laser systems with output power levels up to the tens of watts can be used for these applications, although lower powered laser systems with output power levels in the 10 milliwatt range can be used in microbicidal applications, tissue biostimulation applications, low-level light therapy, and other non-tissue-destructive applications.

A conventional laser system generally includes three primary components: a laser medium that generates the laser light, a power supply that delivers energy to the laser medium in the form needed to excite the same to emit coherent light, and an optical cavity or resonator that concentrates the light to stimulate the emission of laser radiation. Laser emissions can range from ultraviolet wavelengths, visible light wavelengths, to infrared wavelengths, depending on the type of laser medium utilized, and whether the medium comprises one or more gases, chemicals, dyes, metal vapors, and whether the laser is solid state, or semiconductor, etc.

Conventional laser systems suitable for surgical applications are generally comprised of the aforementioned laser energy source and a separate hand-piece coupled thereto that can be manually operated by the practitioner. In a basic implementation, the hand-piece includes a tip assembly comprising an optical fiber that is in optical communication with a waveguide and hence the laser energy source. The output end or surface of the optical fiber directs the emitted laser energy on to a target tissue site, and varying shape configurations can yield different output profiles, including simple circular patterns. The laser emission can be directed at any angle that maximizes operator flexibility and comfort in accessing the target tissue site. The optical pathway can be offset from a connecting cable/handpiece axis using different reflector arrangements.

In many conventional laser devices suitable for medical applications, there is a requirement that the practitioner, clinician or other user of the device "initiate" any new optical fiber integrated into the tip assembly. The general objective of the initiation process is to facilitate the impregnation of certain organic or non-organic materials into the distal portion of the optical fiber that results in at least a portion of the laser energy applied through the optical fiber being partially absorbed and converted into heat.

In one currently known, often used initiation process, an initiation block is provided, such block typically being fabricated from cork, a carbon based organic material. The initiation process is facilitated by initially touching the distal end of the optical fiber to the exposed top surface of the block. Thereafter, the laser is fired, allowing the optical fiber to sink into or burn its way into the block. Then, the optical fiber is pulled from within the block. The laser continues to be fired until the optical fiber has been completely removed from the block. Upon the removal of the optical fiber from block, the laser is fired once into the air, which typically results in the appearance of a glowing distal end portion of the optical fiber. A glowing distal end portion indicates that the initiation has been successful, and that the optical fiber, and hence the tip assembly, is ready for use. Other currently known initiation processes follow a similar protocol, but employ the use of carbon-based organic materials other than for cork (e.g., organic pigments), or non-organic (synthetic), non-metal based pigments.

This known initiation process is intended to facilitate the impregnation of any one of the aforementioned initiating materials into a distal portion of the optical fiber to facilitate the functional objectives described above. However, the primary deficiency arising from the use of these particular initiating materials lies in their inability to create good adhesion or a good chemical bond to the glass during the melting thereof which occurs during the initiation process.

SUMMARY

Some embodiments of the invention include a method of initiating a laser tip assembly comprising providing a laser tip assembly including an uninitiated optical fiber comprising a distal portion including a distal end portion defining a distal, and applying an initiating material to at least a portion of the distal end portion. Further, the method includes operatively coupling the uninitiated optical fiber to a laser source, where the laser source is operative to emit laser energy at prescribed wavelengths and output power ranges. The method also includes firing the laser source for a prescribed time interval which results in the metal component of the initiating material being impregnated into the distal end portion of the optical fiber.

In some embodiments, the method includes the initiating material being applied to the distal end portion from the distal end up to about 3 mm from the distal end. In some further embodiments, the initiating material is applied by dipping at least a portion of the uninitiated optical fiber into initiating material. In some embodiments, the initiating material comprises an enamel material and a base material.

Some embodiments include an enamel material that comprises a mixture of brass particles. In some further embodiments, the base material comprises at least one organic solvent. In some embodiments, the organic solvent comprises at least one of xylene, ethyl benzene, and mineral spirits. In some embodiments, the organic solvent comprises 1% to 10% by weight of xylene, 1% to 5% of ethyl benzene, and 25% to 35% by weight of mineral spirits. In some embodiments, the mixture of brass particles comprises 5% to 35% by weight of copper and 1% to about 5% by weight of zinc. In some embodiments, the enamel material comprises a metal powder or pigment. In some further embodiments, the metal powder or pigment comprises an aluminum powder.

In some embodiments of the invention, the initiating material is at least partially dried. Further, in some embodiments, the initiating material is dried for a time period of between about 5 and about 15 minutes. Some embodiments of the method further comprise cleaning the distal end portion of the optical fiber with a cleaning agent prior to the application of the initiating material. In some embodiments, the cleaning agent comprises isopropyl alcohol. In some further embodiments, the base material is ignitable and flammable in air.

In some further embodiments, the laser source is a diode laser source configured to emit laser energy with a wavelength range of about 400 nm to about 1500 nm and with an output power range of about 0.4 W to about 2.5 W. In some embodiments, the laser source is fired for a time interval in the range of about 10 seconds to about 20 seconds.

Some embodiments of the invention include cleaning the distal end portion of the optical fiber with a prescribed cleaning agent, and inspecting the distal end portion for chips and fractures. In some embodiments, the cleaning agent comprises distilled water.

Embodiments of the invention are best understood by reference to the following detailed description when read in conjunction with the accompanying drawings.

DESCRIPTION OF THE DRAWINGS

These, as well as other features of the invention, will become more apparent upon reference to the drawings wherein.

Common reference numerals are used throughout the drawings and the detailed description to indicate like elements.

DETAILED DESCRIPTION

Some embodiments of the invention include a method of initiating an optical fiber of a tip assembly which employs the use of an initiating material comprising a metal colored enamel, and more particularly a mixture of metal particles at least partially dispersed within at least one flammable (i.e., ignitable) solvent. Some embodiments include the use of embodiments of the aforementioned initiating material in a finished and initiated optical fiber where of the tip assembly can be impregnated with metal particles or flakes. The adhesion or bond of the metal particles or flakes to the optical fiber can be at least equal or superior to that of carbon based materials or non-organic, synthetic, non-metal based pigments impregnated into tips in accordance with existing initiation techniques.

In some embodiments, the initiation process can be completed by the supplier, or the tip assembly manufacturer, or the manufacturer of the medical laser device with which the tip assembly is supplied (i.e., the practitioner, clinician or other end user of the laser device is provided with a pre-initiated tip assembly). In this way, the end user is alleviated from the burden of having to complete the initiation process, thus further avoiding the potential for such process being improperly completed upon the tip assembly.

Figure 1:
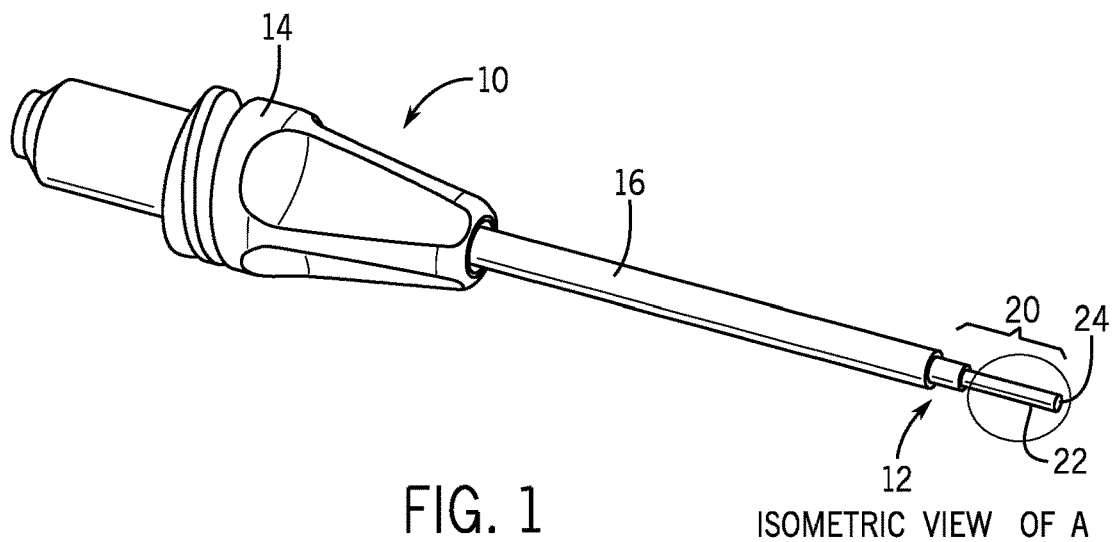
FIG. 1 is a front isometric view showing a tip assembly as subject to the completion of the initiation process in accordance with some embodiments of the invention.
Figure 2:
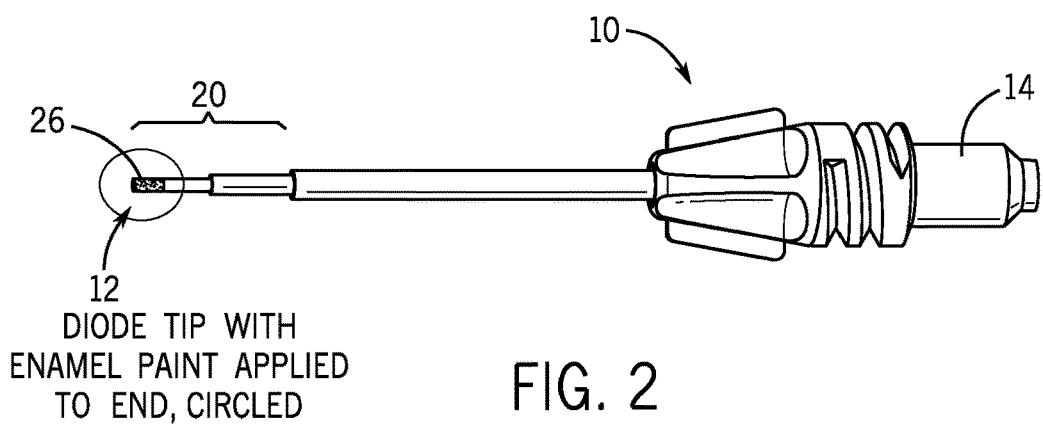
FIG. 2 is a side profile view of the tip assembly shown in FIG. 1, depicting the distal end portion of the optical fiber thereof as painted or coated with the initiating material in accordance with some embodiments of the invention.

Referring now to the drawings for which the showings are for purposes of illustrating embodiments of the invention only, and not for purposes of limiting the same, FIG. 1 depicts a tip assembly 10 which can be subject an initiation process completed in accordance with the invention. In some embodiments, the tip assembly 10 can comprise an elongate optical fiber 12, a ferrule 14, and an elongate, tubular metal sheath or cannula 16 which has a generally circular cross-sectional configuration that protrudes from one end of the ferrule 14. In some embodiments of the invention, the optical fiber 12 can be advanced through the cannula 16, as will be described in more detail below. As is shown in FIG. 2, the end of the ferrule 14 opposite the end having the cannula 16 protruding therefrom can adapted to be operatively coupled to a waveguide 18, which in turn can be operatively coupled to a laser source.

As is apparent from FIGS. 1-4 and as indicated above, in some embodiments, the cannula 16 can accommodate a portion of the optical fiber 12 within the tip assembly 10. More particularly, in some embodiments, the optical fiber 12 can be interfaced to the remainder of the tip assembly 10 such that a distal portion 20 of the optical fiber 12 protrudes from the distal end of the cannula 16 disposed furthest from the ferrule 14. This protruding distal portion 20 of the optical fiber 12 further defines a distal end portion 22, the diameter of which in some embodiments is less than that of the remainder of the distal portion 20. Further, in some embodiments, the distal end portion 22 can define an output surface or distal end 24 of the optical fiber 12. In accordance with known techniques, the optical fiber 12 is can be fabricated from extruded glass (e.g., silica).

As indicated above, in some embodiments, the ferrule 14 of the tip assembly 10 can be adapted to be reversibly coupled and/or engaged to waveguide 18. For example, in some embodiments, the ferrule 14 of the tip assembly 10 can be adapted to be repeatedly engaged and disengaged with the waveguide 18. In some embodiments, the connection of the tip assembly 10 to the waveguide 18 can in turn facilitate the operative coupling of the optical fiber 12 of the tip assembly 10 to the laser source. In this regard, with the tip assembly 10 being interfaced to the waveguide 18, in some embodiments, the firing of the laser source can facilitate the transmission of laser energy to and through the optical fiber 12. Further, to facilitate the completion of the initiation process of the invention which will be described in more detail below, in some embodiments, the laser source can be a diode laser operative in a wavelength range of from about 400 nm to about 1500 nm, and the output power range can be about 0.4 W to about 2.5 W.

In some embodiments of the invention, the initiation method or process of the invention can begin with cleaning of the distal portion 20 of the tip 10, prior to its interface to the hand-piece 12. Some embodiments include a cleaning agent comprising isopropyl alcohol. In other embodiments, other alcohol-based cleaners can be used. In some further embodiments, the cleaning agent can comprise distilled water.

In some embodiments of the invention, the cleaning step can be followed by the application of an energy absorbing initiating material 26 to the optical fiber 12, and in particular to a prescribed section or region of the distal end portion 22 thereof, including the distal end 24. In some embodiments, the initiating material 26 can be an enamel material comprising a mixture of brass (copper and zinc) powder/pigment or flakes in a clear base comprising a solution of organic solvents. In some embodiments, the organic solvents can include xylol (xylene) at a range between about 1% to about 10% by weight; ethyl benzene at a range between about 1% to about 5% by weight; and/or mineral spirits at a range between about 25% to about 35% by weight. In some embodiments, the brass pigment can comprise copper at a range between about 5% to about 35% by weight, and zinc at a range between about 1% by weight to about 5% by weight. However, in some embodiments, the brass powder/pigment included in the initiating material 26 can optionally be substituted with aluminum powder/pigment, or another metal powder/pigment, without departing from the spirit and scope of the invention.

In some embodiments, any initiating material 26 used in the initiation method of the invention will possess certain characteristics or traits. For example, in some embodiments, the characteristic or trait can include the initiating material 26 being capable of adhering to silica. Further, in some other embodiments, the characteristic or trait can include the ability of the initiating material 26 to be biocompatible upon heat decomposition. Further, in some further embodiments, the characteristic or trait can include the ability of the initiating material 26 to react with silica under laser radiation at a wavelength of about 940 nm. In some embodiments, this can create a non-removable, semi-transparent layer within the optical fiber 12 which heats up under laser radiation at the same wavelength of about 940 nm. As the brass, aluminum or other metal component thereof can include a tendency to settle. In some embodiments, for the initiation method, it is important that the initiating material 26 be substantially evenly mixed (to prevent settling at the bottom of any container holding the initiating material 26). In the event that several tip assemblies 10 are to be initiated in series using the initiation method of the invention, in some embodiments, any container holding the initiating material 26 can reside on a plate agitator or a plate shaker to prevent any separation of the initiating material 26.

In some embodiments of the invention, the process used to facilitate the application of the initiating material 26 to the optical fiber 12 of the tip assembly 10 can be a dipping process. More particularly, in some embodiments, the distal end portion 22 of the optical fiber 12 can be dipped by placing the distal end 24 first into the initiating material 26 to a depth in a range of from about 1 mm to about 3 mm. The tip assembly 10 can then be placed into a dryer rack, with the dipped distal end portion 22 of the optical fiber 12 pointing downward so that the initiating material 26 can collect on the distal end 24. In some embodiments, without acceleration, the initiating material 26 can take about 5 minutes to dry, although about 15 minutes of time can be taken to ensure the drying is substantially complete. However, in some embodiments, a heated air dryer or a heat gun can be used to accelerate the drying process. In this regard, the air dryer must not remove any initiating material 26 from the distal end portion 22 of the optical fiber 12. In some embodiments, the dryer rack can be configured to simultaneously hold any number of tip assemblies 10. In some embodiments, after the initiating material 26 has dried, an inspection can optionally be completed. For example, the inspection process can include capturing an image of the dried initiating material 26 under 100× magnification to ensure the integrity and completeness thereof. The encircled region of FIG. 2 depicts the dried initiating material 26 as coated onto distal end 24 and a segment of about 2-3 mm of the of the distal end portion 22 of the optical fiber 12 extending from the distal end 24.

Some embodiments include a next step of the initiating method where the tip assembly 10 is operatively coupled to the waveguide 18. As previously described, this coupling facilitates the operative coupling of the optical fiber 12 of the tip assembly 10 to the laser source. In some embodiments, the laser source can be set to an output power range of about 0.4 W to about 2.5 W continuous wave (measured at the output of the waveguide 18 with a calibrated power meter and sensor). In some embodiments of the invention, the particular output power selected can be understood to be dependent on the diameter and other dimensional parameters of the optical fiber 12 of the tip assembly 10 to be initiated.

In some embodiments of the invention, a subsequent step of the initiation method can include the laser source being fired for a time period of about 15 sec (+/− about 5 sec) to deliver energy to the distal end 24 of the tip 10. During this initiation, the initiating material 26 applied to the distal end portion 22 of the optical fiber 12 can ignite and burn-off. In particular, in some embodiments, the initiating process can burn off nearly 100% of the solvents included in the aforementioned clear base of the initiating material 26. In some embodiments of the invention, during the initiation process, the laser energy can be at least partially absorbed in the initiating material 26 (e.g., about 5% absorption up to about 95% absorption). In some embodiments, the absorbed light energy can ignite the solvents of the clear base. In some embodiments, ignition and combustion can melt portions of the optical fiber 12, and impregnate the optical fiber 12 with the metal (e.g., brass, aluminum, etc.) powder/pigment of the initiating material 26. In some embodiments, the initiated or conditioned tip assembly 10, and in particular that segment of the distal end portion 22 of the optical fiber 12 thereof originally covered or coated by the initiating material 26, can be permanently modified so that the energy applied through the optical fiber 12 is partially absorbed and converted to heat.

Figure 3:
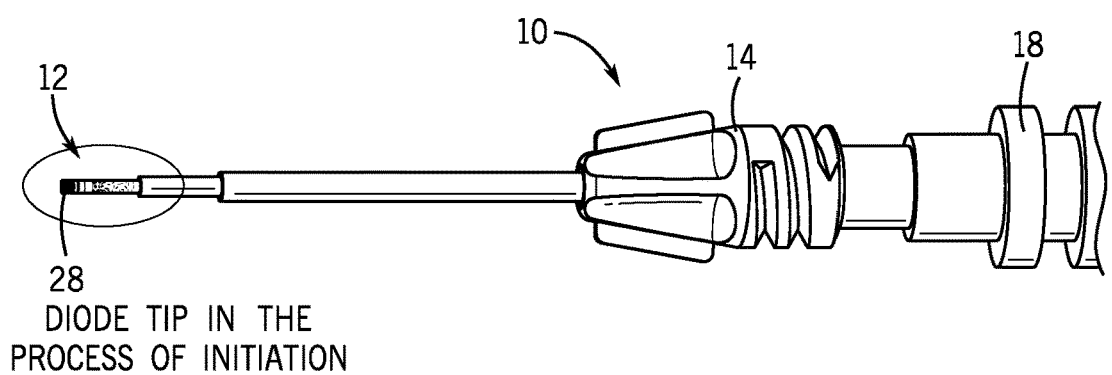
FIG. 3 is a side profile view of the tip assembly similar to that shown in FIG. 2, depicting the optical fiber thereof during the process of initiation as resulting from the firing of a laser energy source operatively coupled to the tip assembly in accordance with some embodiments of the invention.

In some embodiments, the encircled region of FIG. 3 depicts the distal end portion 22 of the optical fiber 12 in the process of initiation in accordance with various embodiments of the initiation method of the invention. In some embodiments of the invention, a visual indication of the success of the initiation process can include the ability to observe a glow 28 (e.g., an orange glow) at the distal end portion 22 of the optical fiber 12.

Figure 4:
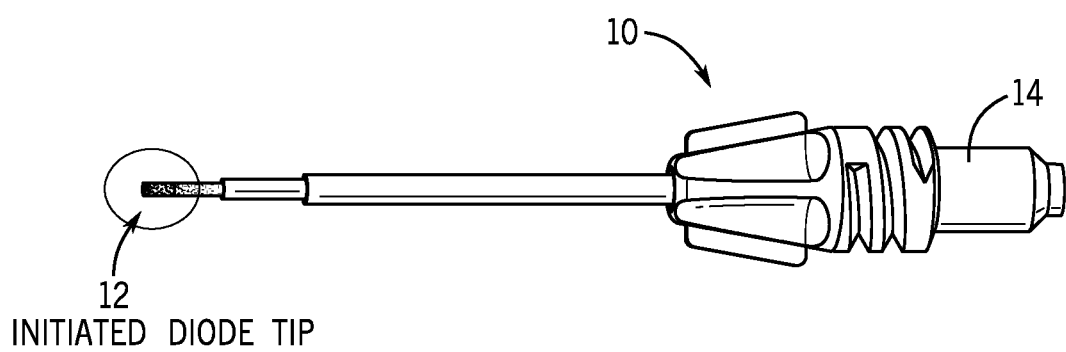
FIG. 4 is a side profile view of the tip assembly similar to that shown in FIGS. 2 and 3, depicting the optical fiber thereof subsequent to the completion of the initiation process thereon in accordance with some embodiments of the invention.

In some embodiments of the invention, following the initiation as described above in relation to FIG. 2, the optical fiber 12 of the tip assembly 10 can be allowed to cool for several seconds. Thereafter, residual burned materials can be removed from the distal end portion 22 of the optical fiber 12 with a dry tissue or sponge, or with distilled water, or any other suitable cleaning solution such as isopropyl alcohol, acetone, other alcohols and organic solvents. The encircled region of FIG. 4 depicts the distal end portion 22 of the tip 10 subsequent to the completion of the initiation process in accordance with some embodiments of the initiation method.

In some embodiments of the invention, subsequent to the completion of the aforementioned cleaning step, the initiated or conditioned tip assembly 10, and in particular the optical fiber 12 thereof, can be optionally inspected for chips or fractures at the distal end portion 22, including the distal end 24. The optional inspection process can include capturing an image of the conditioned end of the optical fiber 12 under 100× magnification. In some embodiments, bubbling or bulging of the distal end portion 22 of the optical fiber 12 and imbedded brass, aluminum or other metal is normal can occur, and may be observed during the inspection.

Some other embodiments can include an initiation process where the drying step is eliminated, and where the firing of the laser source can occur while the initiating material 26 is still wet. In some embodiments, the firing of the laser can potentially occur while the distal end portion 22 of the optical fiber 12 is still dipped within a container of the initiating material 26.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. An optical fiber preparation system comprising: providing an optical fiber including a distal portion including a distal end portion including an output surface, the output surface configured to emit laser energy when coupled to a laser source; coupling the optical fiber to a waveguide; depositing an initiating material onto at least a portion of the output surface of the distal end portion, the initiating material including powdered or flaked metal; and transmitting the laser energy through the optical fiber to the output surface, wherein the powdered or flaked metal of the initiating material is impregnated into at least a portion of the optical fiber following at least some melting of portions of the optical fiber after receiving the laser energy; and wherein the initiating material includes at least one organic solvent that is combusted by the laser energy causing the melting of the optical fiber, the melting causing or facilitating the impregnation and chemical bonding of the powdered or flaked metal to the optical fiber.

2. The system of claim 1, wherein the initiating material includes a characteristic or trait of adhering to silica of the optical fiber, and creating a semi-transparent layer within the optical fiber by reaction with the silica when the laser energy has a wavelength of 940 nm.

3. The system of claim 2, wherein the optical fiber heats up under irradiation with the laser energy having a wavelength of 940 nm.

4. The system of claim 1, wherein the initiating material is deposited onto the distal end portion from the distal end up to 3 mm from the output surface.

5. The system of claim 1, wherein the initiating material is applied by dipping or painting.

6. The system of claim 1, wherein the metal contains copper and zinc.

7. The system of claim 6, wherein the metal includes 5% to 35% by weight of copper, and 1% to 5% by weight of zinc.

8. The system of claim 1, wherein the metal contains aluminum.

9. The system of claim 1, wherein the powdered or flaked metal is aluminum powder or flake.

10. The system of claim 1, wherein the initiating material is partially dried following deposition.

11. The system of claim 1, wherein the distal end portion of the optical fiber is cleaned with a cleaning agent prior to deposition of the initiating material, the cleaning agent comprising at least one of distilled water and isopropyl alcohol.

12. The system of claim 1, wherein the laser energy is emitted from a diode laser with a wavelength range of 400 nm to 1500 nm, the laser energy power range is 0.4 W to 2.5 W, and the laser energy is applied for a time interval in the range of 10 seconds to 20 seconds.

* * * * *